(12) United States Patent
Scholz et al.

(10) Patent No.: US 6,461,857 B1
(45) Date of Patent: Oct. 8, 2002

(54) PRODUCING WATER-SOLUBLE YEAST EXTRACT BY ADDING PEROXIDE TO GROWING YEAST CELLS

(75) Inventors: Durant B. Scholz, Chestnut Ridge, NY (US); Derek Parish, Middletown, NJ (US); Hans Schaeffer, Bethesda, MD (US)

(73) Assignee: Arch Personal Care Products, L.P., South Plainsfield, NJ (US)

( * ) Notice: Subject to any disclaimer, the term of this patent is extended or adjusted under 35 U.S.C. 154(b) by 0 days.

(21) Appl. No.: 09/619,222

(22) Filed: Jul. 19, 2000

(51) Int. Cl.$^7$ .......................... A61K 6/00; C12P 1/100; C12N 1/00; C12N 1/14; C12N 1/18
(52) U.S. Cl. .................... 435/255.1; 424/195.16; 424/401; 435/41; 435/252.1; 435/255.7; 435/911
(58) Field of Search .................. 424/439, 520, 424/93.21, 93.51, 195.15, 255.1, 195.16, 400, 401; 435/172.3, 921, 252.1, 259, 254.1, 255.1, 255.21, 255.7, 911

(56) References Cited

U.S. PATENT DOCUMENTS

| | | | |
|---|---|---|---|
| 2,239,345 A | 4/1941 | Sperti | 167/74 |
| 2,320,478 A | 6/1943 | Sperti | 167/91 |
| 3,909,352 A | 9/1975 | Akiyama et al. | 195/28 R |
| 4,618,578 A | 10/1986 | Burke et al. | 435/68 |
| 4,769,328 A | 9/1988 | Murray et al. | 435/68 |
| 5,182,208 A | 1/1993 | Johnson et al. | 435/254 |
| 5,356,809 A | 10/1994 | Johnson et al. | 435/255.1 |
| 5,643,587 A | 7/1997 | Scancarella et al. | 424/401 |
| 5,676,956 A | 10/1997 | Duffy et al. | 424/401 |
| 5,776,441 A | 7/1998 | Scancarella et al. | 424/61 |

*Primary Examiner*—David M. Naff
*Assistant Examiner*—Deborah K. Ware
(74) *Attorney, Agent, or Firm*—Dale Lynn Carlson; Wiggin & Dana LLP

(57) ABSTRACT

Provided is a process of and product resulting from adding a sub-lethal amount of a peroxide to a growing culture of yeast, observing the change in absorbance of the culture at 256 nm as a measure of the injury occurring to the yeast cells, and, upon reaching a predetermined absorbance value, purifying the water-soluble yeast extract from the peroxide containing yeast culture. The resulting product has at least 1.5 respiratory units per mg dry weight and has significantly increased amounts of 15, 25 and 55 kD molecular weight products compared to a Live Yeast Cell Derivative as determined by SDS slab gel electrophoresis. This product can be combined with a cosmetically acceptable carrier to provide a composition suitable for topical application to the skin.

8 Claims, 5 Drawing Sheets

PRODUCING WATER-SOLUBLE YEAST EXTRACT BY ADDING PEROXIDE TO GROWING YEAST CELLS

BACKGROUND OF THE INVENTION

1. Field of the Invention

The present invention relates to an improved yeast extract for use in the cosmetic arts, which maintains the cell-stimulatory effects of the prior art yeast extracts, while providing additional photo-protective effects.

2. Description of the Prior Art

The aging process is accompanied by the slowing of physiologic life processes. Foremost among these is the decrease in the body's ability to maintain a hemostatic environment when faced with a chronic, daily onslaught of stresses. Aging results in part from damage to cells and tissues by a variety of factors both internal and external, natural and artificial. Our bodies have evolved genetically to recognize these damages and instigate their repair, and in some cases degrade the resulting abnormal proteins. The affects of the aging progression become evident in our skin.

Yeast, because its processes closely resemble those of individual human cells, has become a mainstay of biochemical research. Its genome completely defined, yeast is an ideal tool with which to study cellular defense mechanisms. Man has commercially harnessed the production capacity of yeast to produce a variety of pharmaceutical and cosmetic active ingredients. Within the cosmetic industry, one driving force for harnessing yeast has been the movement away from animal-derived active ingredients for ethical, regulatory or safety concerns.

Cellular damage provokes defensive responses from cells. Exposure to heat, UV radiation, pollutants or other adverse conditions stimulates the generation of defensive gene products. These defensive gene products can promote cell respiration, cell proliferation or cell viability in the face of adverse conditions.

George Sperti found that yeast cells could be stimulated by heat, UV radiation, x-rays or chemical injury to produce stress-induced defensive factors, later termed "heat shock proteins". These heat shock proteins (Hsp) might be more appropriately called "stress response proteins". Sperti's research has shown that yeast, rat, mouse, chick and various bacterial cells all produce stress factors upon injury that could stimulate cellular repair in cultured cells derived from other species. See U.S. Pat. No. 2,239,345. Heat shock proteins either replace cellular functions disabled by the stress or act as molecular chaperones protecting native structures typically by modifying protein folding.

Viable yeast cultures exposed to UV light of a specified wavelength (286 nm) produce the isolate known as Live Yeast Cell Derivative (LYCD). LYCD has seen broad application within the pharmaceutical and cosmetic industries. Whitehall Labs has used LYCD as a wound-healing agent in their anti-hemorrhoidal preparations. Studies have shown that LYCD will increase the rate of wound healing in humans where the wounds were a result of either thermal or mechanical damage. See Goodson, et al., Augmentation of some aspects of wound healing by "skin respiratory factor". J. Surg. Res. (1976) 21. 125–129. The rate of wound healing is associated with an increase in collagen synthesis, which is believed to be associated with elevated fibroblast respiration.

The ability of LYCD to promote fibroblast activity has accounted for its popular use in cosmetics. Several U.S. patents revolve around the use of LYCD for moisturizing or improving skin's appearance. See, for instance, U.S. Pat. No. 5,643,587 or 5,676,956 or 5,776,441. It is thought that by increasing collagen and elastin synthesis, LYCD acts as an internal moisturizer binding water in the skin. Cosmetic application of LYCD increases oxygen uptake by cells and stimulates repair, in turn slowing visible signs of aging. LYCD is capable of preventing the accumulation of stress-damaged proteins in the sells and in the body by initiating their breakdown.

It has often been discussed that oxygen is a "dangerous friend". Oxidation is one of the major mechanisms of aging, both intrinsic and extrinsic. Yeast possesses the same mechanism for combating oxidative stress as higher eukaryotes, containing distinct transcriptional activators which respond to hydrogen peroxide and superoxide anions. J. Gen. Microbiol. 139 501–507. Recent work has identified over 100 proteins that are stimulated by sub-lethal doses of hydrogen peroxide. J Biol. Chem. (1998) 273(34) 2280–2289.

SUMMARY OF THE INVENTION

It is therefore an object of the present invention to provide a yeast cell extract for use in the cosmetic arts which provides the same or better cell stimulatory effects of the prior art while providing new protection from cellular damage caused by activated oxygen species and/or UV light.

It is a further object of the present invention to provide a cosmetic composition with properties of cell stimulation and protection from cellular damage caused by activated oxygen species and/or UV light.

It is yet another object of the present invention to provide a method of preparing a yeast cell extract which has the properties of cell stimulation and protection from cellular damage caused by activated oxygen species and/or UV light.

These objects are achieved by a process of and product resulting from adding a sub-lethal amount of a peroxide to a growing culture of yeast, observing the change in absorbance of the culture at 256 nm as a measure of the injury occurring to the yeast cells, and, upon reaching a predetermined absorbance value, purifying the water-soluble yeast extract from the peroxide containing yeast culture. The resulting product has at least 1.5 respiratory units per mg dry weight and has significantly increased amounts of 15, 25 and 55 kD molecular weight products compared to a Live Yeast Cell Derivative as determined by SDS slab gel electrophoresis. This product can be combined with a cosmetically acceptable carrier to provide a composition suitable for topical application to the skin.

As used herein, "respiratory unit" is defined as the quantity of PTYE which increases oxygen consumption of 1 mg of rat abdominal tissue by 1% in a one hour period when measured by Warburg manometry.

As used herein, "cosmetically acceptable carrier" includes those carriers known for use in lotions, creams, toners or masks for skincare, those carriers known for use in decorative products such as lipsticks, concealers, foundations or powders and those caries known for use in leave-in haircare preparations such as tonics, gels and lotions. The yeast extracts of the instant invention can be used to replace LYCD in any cosmetic formulation.

As used herein, "sub-lethal amount" means an amount that provides a kill rate of less than 90% of the viable cells. A minimum effective concentration of the peroxide is one which produes measurable increase in absorbance of the culture of light having a wavelength of 256 nm.

As used herein, "peroxide" means any chemical compound containing a peroxide group. Furthermore, an embodiment of the invention uses in place of the peroxide nonperoxide chemical compounds that provide oxidative stress. Oxidative stress is the damaging effects of oxidation caused by reactive oxygen species. Examples of nonperoxide chemical compounds that provide oxidative stress include superoxide anion, hydroxyl radical and nitric oxide.

DETAILED DESCRIPTION OF PREFERRED EMBODIMENTS

Our interest in the effects of oxidative stress led us to introduce sub-lethal doses of $H_2O_2$ into yeast cultures. The yeast cultures are then observed for spectrophotometric absorbance at 256 nm. This absorbance indicates changes in the nucleotide composition within the cells as a result of "injury". Once the absorbance exceeds a value corresponding to a final extract having at 1.5 respiratory units/mg, the yeast culture is harvested. The water-soluble fraction from the treated yeast is then isolated by centrifugation, concentrated and assayed for biological activity. This is similar to the process used to produce LYCD. This new extract is called Peroxide Treated Yeast Extract (PTYE).

PTYE shows similar properties to LYCD in terms of pH and respiratory units as determined by spectrophotometric absorbance at 256 nm. Because of the oxidative stress of $H_2O_2$ used to stimulate the yeast in the production of PTYE, a new spectrum of anti-oxidant activity is evident. PTYE increases cell respiration and enhances protection from oxidative stress and UV radiation. Interestingly PTYE reacts positively to a Biuret assay whereas LYCD does not.

Figure 1:
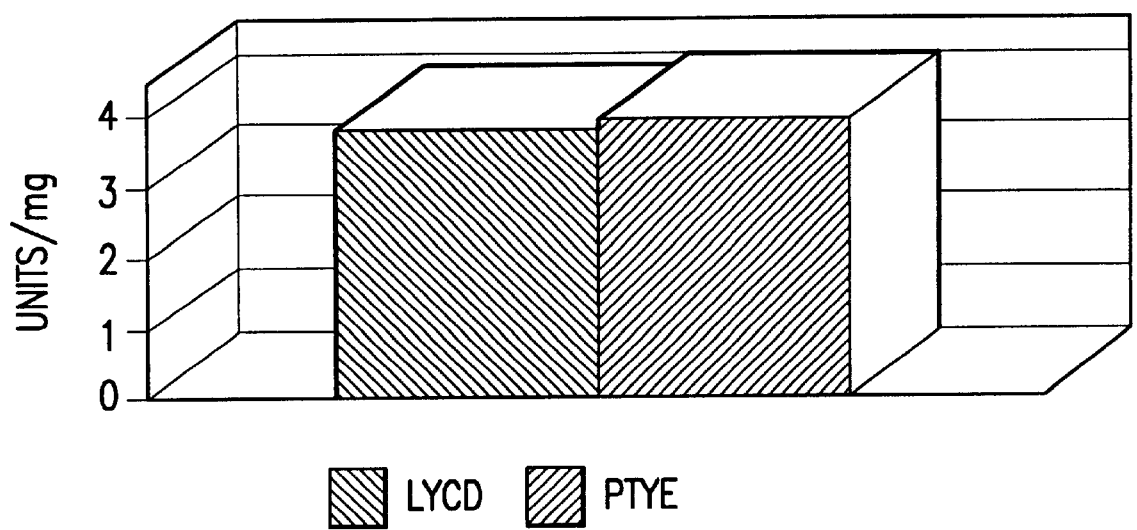
FIG. 1 is comparison of the respiratory units of equal amounts of LYCD and a yeast extract of the instant invention.

We compared the effect of PTYE and LYCD on isolated human fibroblasts. The fibroblasts were prepared and aerated. Test solutions were then added and the difference in the rate of oxygen consumption was used to calculate Respiratory Units. For the purposes of our analysis, we submitted a sample of LYCD as a 25% aqueous solution and PTYE also as a 25% aqueous solution. The analysis results are shown in FIG. 1. Having determined that the level of Respiratory Units remained constant regardless of the mechanism of insult offered to the yeast culture, we continued to investigate other properties for differences.

Figure 2:
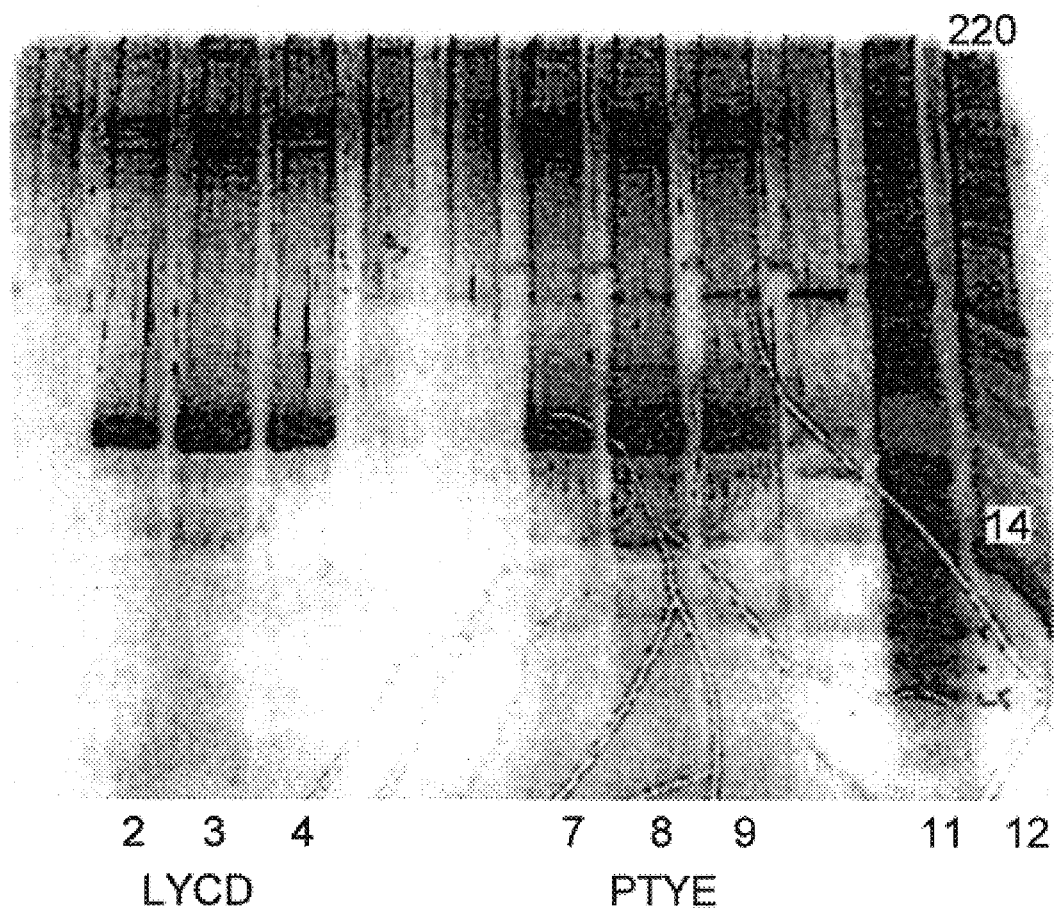
FIG. 2 is a photograph of a stained SDS gel on which the components of LYCD and a yeast extract of the instant invention have been partially separated according to molecular weight.
Figure 3:
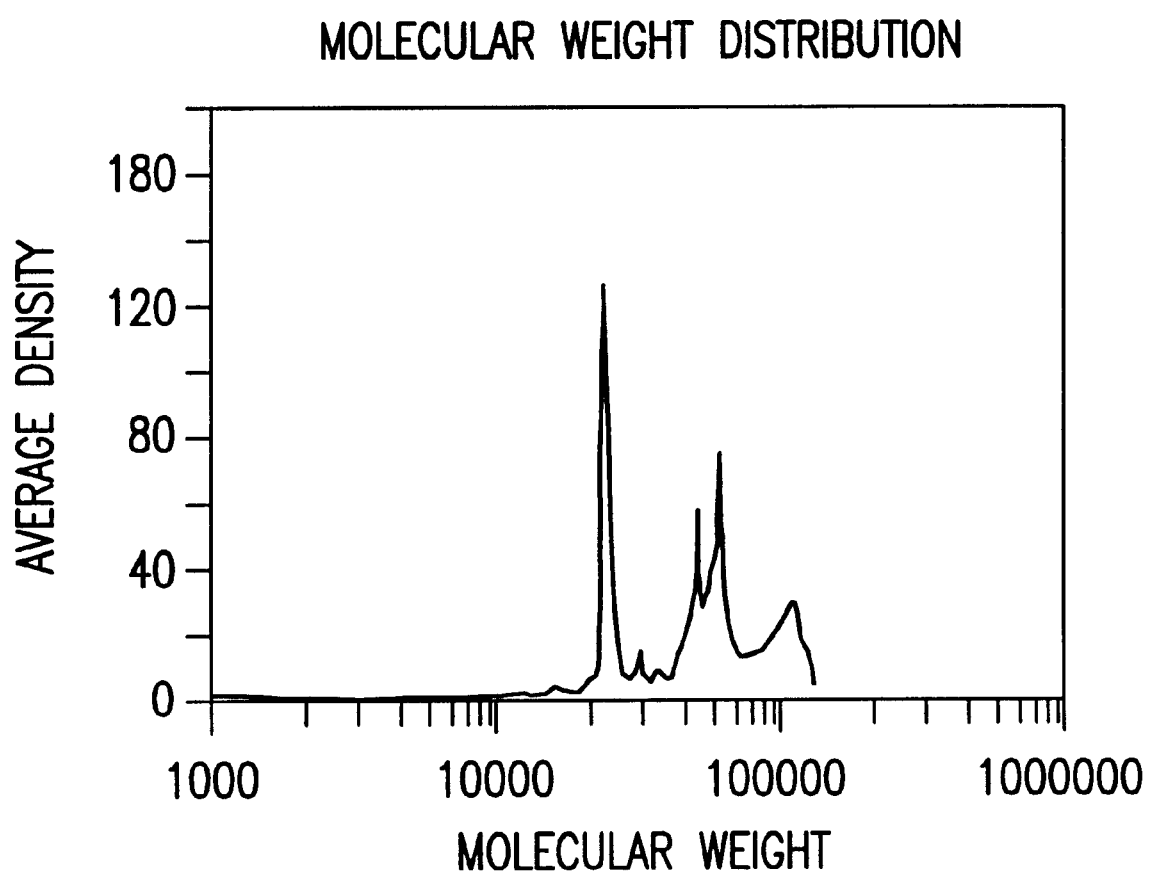
FIG. 3 is a graph of the molecular weight distribution of LYCD from the stained SDS gel of FIG. 2.
Figure 4:
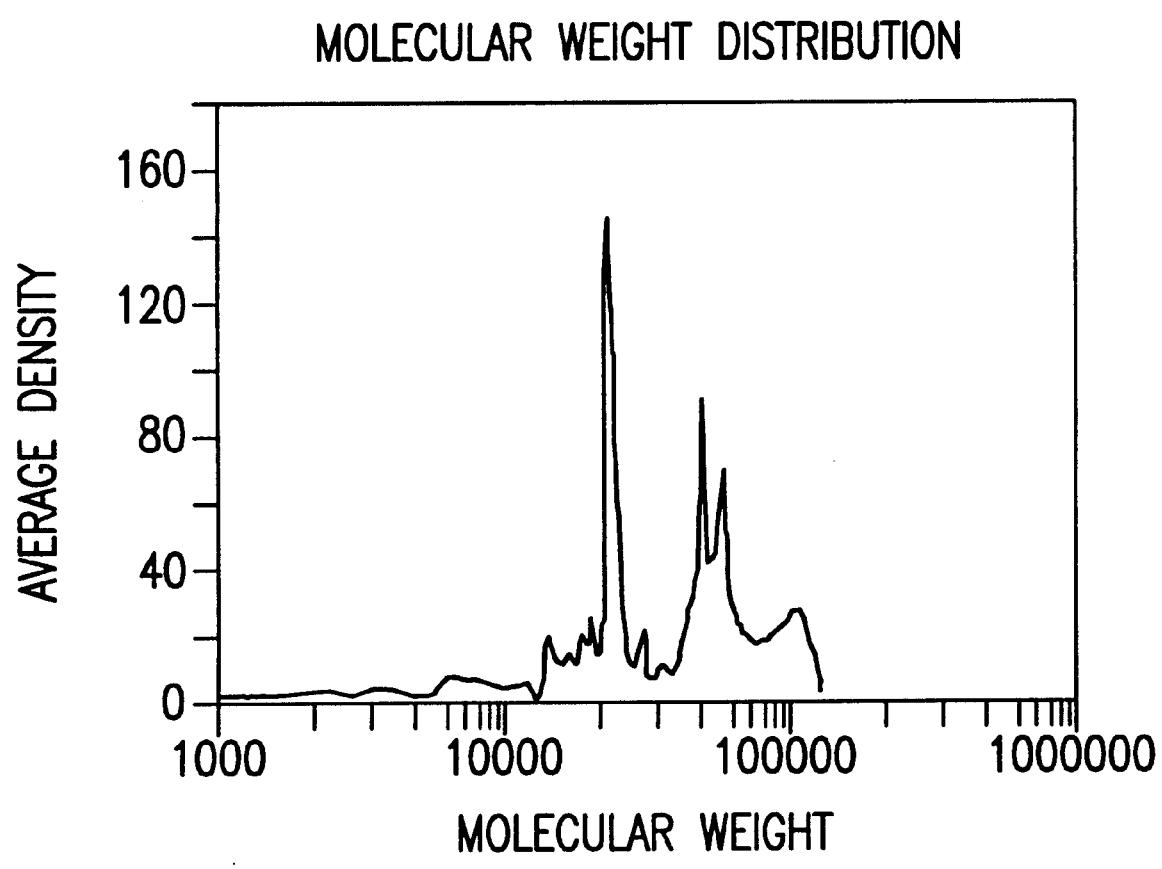
FIG. 4 is a graph of the molecular weight distribution from the stained SDS gel of FIG. 2 of a yeast extract of the instant invention.

Believing that different insults might induce the production of other gene products, samples of LYCD and PTYE were run on an SDS slab gel electrophoresis to determine the distribution of molecular weights of the pool of proteins in the samples. Samples were diluted by weight to 5 mg/ml in SDS Boiling Buffer and the tubes placed in a boiling water bath for 5 minutes to insure dissolution. FIG. 2 shows the actual gel electrophoresis and FIGS. 3 and 4 show the molecular weight versus silver stain density. There is a clear decrease in the bands occurring between 15 and 25 kD and with the band occurring at 55 kD. There do not seem to be any bands present in the LYCD sample that are not present in the PTYE sample.

Figure 5:
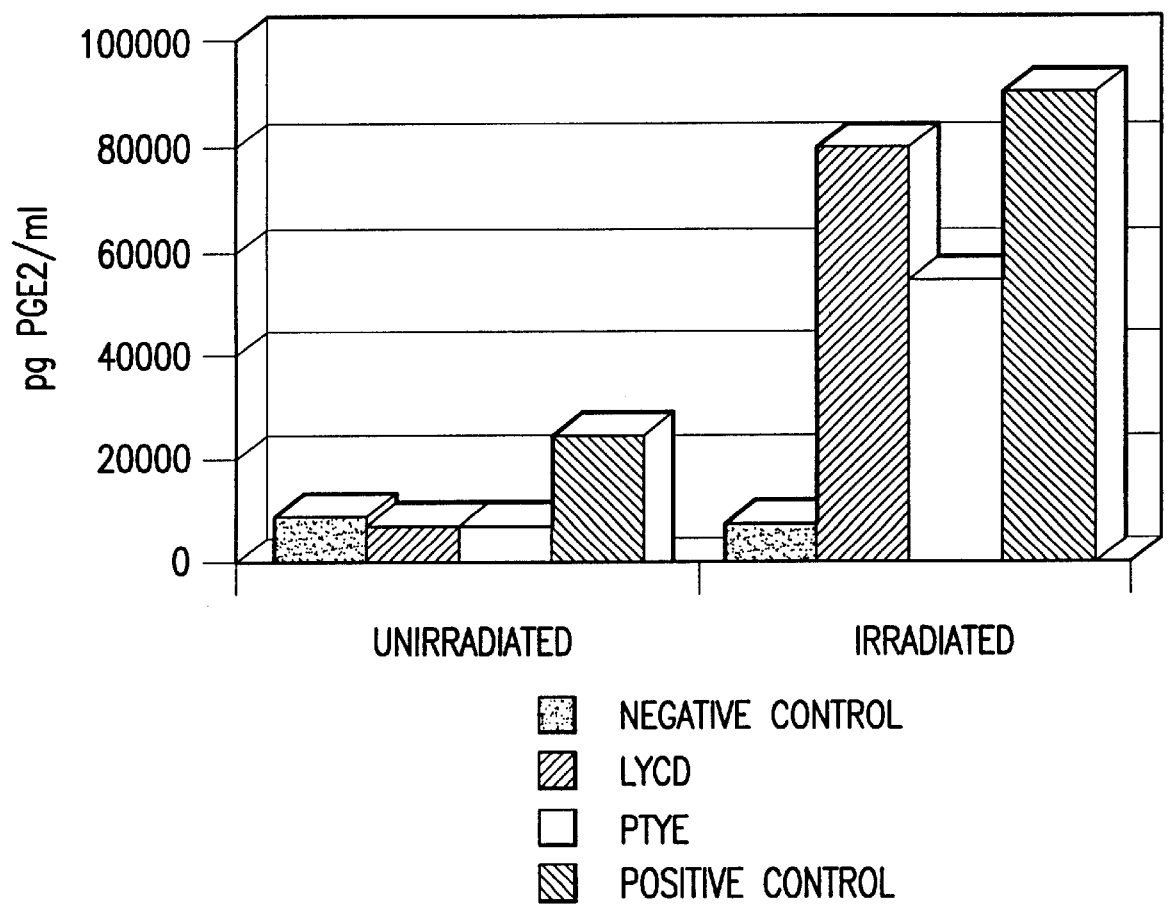
FIG. 5 shows a comparison of the ability of LYCD and a yeast extract of the instant invention to inhibit $PGE_2$ synthesis in irradiated tissue.

Using Human Skin Equivalents (MatTek Corp., Ashland, Mass.) exposed to 31.5 $mJ/cm^2$ UVA/UVB radiation, Prostaglandin $E_2$ ($PGE_2$) synthesis was measured. Unprotected irradiated tissuew generated approximately 90,000 pg/ml of $PGE_2$. By way of comparison, tissue treated with LYCD (0.7% w/w active) and irradiated produced an average of 79,139 pg/ml $PGE_2$. PTYE (0.7% w/w active) reduces $PGE_2$ to an average of 54,490 pg/ml. See FIG. 5. The significant protective effects would seem to indicate that one or more of the uncharacterized gene products induced by $H_2O_2$ treatment offers protection against UVA/UVB induced cell damage.

It is clear that insulting yeast cultures with peroxide produces a product that is equivalent to LYCD in terms of its ability to stimulate cellular oxygen uptake. This equivalence indicates that PTYE is capable of producing the same cosmetically desirable effects as LYCD. Additionally, peroxide induces the production of some soluble protective factors yet to be identified which would seem to be stress response factors.

In another embodiment of the method of producing PTYE, yeast cultures (10 mg *Saccharomyces cerevisiae* per 100 ml media) are brought to viability in a Yeast-Extract Dextrose Medium (YED) with thorough aeration under controlled temperature conditions (30° C.±2). The living yeast cells are then subjected to an injury process such as a sub-lethal dosage (0.4–14.7 mM) of $H_2O_2$. The cells respond to the debilitating effects of the $H_2O_2$ by producing various protective substances. The injury process is continued until the complex biochemical protective mechanisms are complete, a process which can take up to several days. Absorbance by the culture of 256 nm wavelength light is monitored throughout the fermentation process. When the absorbance increases beyond that which corresponds to the required 1.5 respiratory units/mg, the process is halted. The absorbance value which corresponds to 1.5 respiratory units/mg of the final extract can be determined empirically for any particular set of fermentation conditions. Breaking down the yeast cell walls utilizing a proteolytic enzyme stops the fermentation. The bulk of the insoluble cell wall material is removed by centrifugation, leaving cellular protoplasm behind. The protoplasmic derivative is then concentrated and assayed for biological activity in respiratory units.

Other oxidative materials, which can generate the superoxide anion, the hydroxyl radical and nitric oxide can also be used to oxidatively stress yeast cultures and produce PTYE. The amounts of these other oxidative materials used to induce injury may vary, however they must be added in concentrations which will not cause more than a 90% loss in viability of *Saccharomyces cerevisiae* cells present.

Although the invention has been described through particular embodiments, the invention is not limited to those embodiments, but encompasses variations apparent to those of skill in the art and the full breadth of the claims given below.

We claim:

1. A method of producing a water-soluble yeast extract comprising:
   (a) providing a growing culture of yeast cells,
   (b) adding a sub-lethal amount of peroxide to the growing culture, (c) observing absorbance of the peroxide containing culture at 256 nm, and (d) upon reaching a value of absorbance at 256, purifying the water-soluble yeast extract from the peroxide containing culture.

2. The method of claim 1, wherein the peroxide is hydrogen peroxide.

3. The method of claim 2, wherein the sub-lethal amount of peroxide is from about 0.1% by weight to about 2.0% by weight based upon the total weight of the growing culture.

4. The method of claim 3, wherein the sub-lethal amount of peroxide is from 0.7% by weight based upon the total weight of the growing culture.

5. The method of claim 1, wherein the step of purifying comprises the separation of water insoluble components of the peroxide containing culture from the water-soluble yeast extract.

6. The method of claim 5, wherein the separation is achieved by filtration.

7. The method of claim 5, wherein the separation is achieved by centrifugation.

8. A method of producing a water-soluble yeast extract comprising:

(a) providing a growing culture of yeast cells, (b) adding a sub-lethal effective amount of peroxide to the growing culture, (c) exposing the growing culture to a sub-lethal effective amount of ultra-violet radiation, (d) observing absorbance of the peroxide containing culture at 256 nm, and (e) upon reaching a value of absorbance at 256 nm, purifying the water-soluble yeast extract from the peroxide containing culture, wherein the combined amount of peroxide added and exposure of ultra-violet radiation are sub-lethal to the culture.

* * * * *